US006978040B2

(12) United States Patent
Berestov

(10) Patent No.: US 6,978,040 B2
(45) Date of Patent: Dec. 20, 2005

(54) OPTICAL RECOVERY OF RADIOGRAPHIC GEOMETRY

(75) Inventor: Alexander Leonidovich Berestov, San Jose, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 800 days.

(21) Appl. No.: 10/021,245

(22) Filed: Dec. 19, 2001

(65) Prior Publication Data

US 2003/0113006 A1  Jun. 19, 2003

(51) Int. Cl.$^7$ .............................................. G06K 9/00
(52) U.S. Cl. ..................... 382/131; 382/154; 378/23
(58) Field of Search ...................... 382/128–134, 382/154, 159, 169–173, 178, 181, 191–196, 382/209, 219, 237, 240, 255, 260, 274, 275, 382/285, 295, 299, 305; 378/23, 2, 62; 600/426; 250/455

(56) References Cited

U.S. PATENT DOCUMENTS

| | | | | |
|---|---|---|---|---|
| 3,843,225 A | | 10/1974 | Kock et al ..................... | 350/3.5 |
| 3,940,619 A | * | 2/1976 | Ellingson et al. .............. | 378/23 |
| 4,087,837 A | * | 5/1978 | Geluk ............................ | 378/2 |
| 4,246,483 A | | 1/1981 | Weiss et al. .................. | 250/445 |
| 4,513,433 A | | 4/1985 | Weiss et al. .................... | 378/2 |
| 4,516,261 A | | 5/1985 | Harding et al. ................ | 382/6 |
| 4,903,204 A | * | 2/1990 | Dobbins, III ................ | 382/255 |
| 5,359,637 A | | 10/1994 | Webber ......................... | 378/2 |
| 5,668,844 A | | 9/1997 | Webber ........................ | 378/2 |
| 5,872,828 A | * | 2/1999 | Niklason et al. .............. | 378/23 |
| 6,006,126 A | * | 12/1999 | Cosman ....................... | 600/426 |
| 6,081,577 A | * | 6/2000 | Webber ........................ | 378/23 |
| 6,801,597 B2 | * | 10/2004 | Webber ........................ | 378/62 |

OTHER PUBLICATIONS

Alexander L. Berestov, "Stereo Fundus Photography: Automatic Evaluation of Retinal Topography," Stereoscopic Displays and Virtual Reality Systems VII, Proceedings of the SPIE 3957, 50-59 (2000).
Alexander Berestov, "Stereoscopic X-Ray Image Processing," Medicine Meets Virtual Reality 2001, 53-59 (2001).
L. A. Feldcamp, L. C. Davis & J. W. Kress, "Practical Cone-Beam Algorithm," Optics and Image Science, J. Opt. Soc. Am. 1, 612-619 (1984).

(Continued)

*Primary Examiner*—Daniel Miriam
*Assistant Examiner*—Seyed Azarian
(74) *Attorney, Agent, or Firm*—Fitzpatrick, Cella, Harper & Scinto

(57) ABSTRACT

Processing of up to a plurality of radiographic images of a subject, includes the capture of at least two visible light images of the subject, two or more of the visible light images in correspondence to at least one radiographic image. The visible light images are captured by one or more visible light cameras, each visible light camera in a known geometric relation to the radiographic source. Radiographic geometry of each radiographic image is calculated relative to the radiographic source and the subject through stereoscopic analysis of the visible light images and through reference to the known geometric relation between the one or more visible light cameras and the radiographic source. Three-dimensional radiographic information on the subject is generated and manipulated by processing the up to a plurality of radiographic images based on the recovered radiographic geometry.

40 Claims, 11 Drawing Sheets

OTHER PUBLICATIONS

David G. Grant, "Tomosynthesis: A Three-Dimensional Radiographic Imaging Technique," IEEE Trans. Biomed. Eng. 19, 20-28 (1972).

Richard L. Webber, Alexander Berestov, and Jeffrey W. Duryea, "Elimination of Volume Anisotropy in Tomosynthesis Through Biorthogonal Merging of Reconstructions Produced from Contiguous Projections," Medical Imaging, Proceedings of the SPIE 4320, 681-687 (2001).

Ashoke S. Talukdar & David L. Wilson, "Modeling and Optimization of Rotational C-Arm Stereoscopic X-Ray Angiography," IEEE Transactions on Medical Imaging 18, 604-616 (1999).

Andrew Woods, Tom Docherty & Rolf Koch, "Image Distortions in Stereoscopic Video Systems," Stereoscopic Displays and Applications IV, Proceedings of the SPIE 1915, 36-48 (1993).

"Radionics: The Optical Tracking System" (visited Dec. 12, 2001) <http://www.radionics.com/products/frameless/ots.shtml>.

Radionics: OTS™ Software Version 3.0" (visited Dec. 12, 2001) <http://www.radionics.com/products/frameless/ots3.shtml>.

SPIE International Symposium On Medical Imaging 2001: Technical Program Updates/Summary Digest 7 (2001).

* cited by examiner

OPTICAL RECOVERY OF RADIOGRAPHIC GEOMETRY

BACKGROUND OF THE INVENTION

1. Field of the Invention

The present invention concerns radiographic imaging and in particular concerns the use of an optical camera system to recover the radiographic geometry of a radiographic system, and the use of the recovered radiographic geometry to generate and manipulate three-dimensional radiographic information from radiographic images.

2. Description of the Related Art

Radiographic imaging provides a valuable diagnostic tool with both medical and industrial applications. From standard two-dimensional radiographic images, three-dimensional radiographic information can be generated. For example, stereoscopic x-ray imaging techniques process a pair of radiographic images taken from different positions relative to a subject, and generate images of the subject that appear to be three-dimensional when viewed with the proper equipment. As another example, tomosynthesis synthesizes images of internal slices of a subject at specific depths into the subject by combining multiple radiographic images of the subject taken from different positions relative to the subject.

To generate and manipulate three-dimensional radiographic information from multiple radiographic images, the radiographic geometry must be known. In particular, it is necessary to know the exact geometrical relationship between the x-ray source, the subject of the x-ray, and the x-ray sensor. The radiographic geometry provides information used for processing and generating three-dimensional radiographic information such as correcting distortions in radiographic images for stereoscopic x-ray imaging, combining radiographic images when forming tomographic slices, and performing volume reconstruction.

In conventional systems, the radiographic geometry of the system is obtained through precise measurements and calibration of the x-ray source, the subject and the x-ray sensor. The requirement that these measurements be precise throughout the process of obtaining the multiple radiographic images often prevents the use of these systems in situations where it is difficult to obtain or maintain the geometry. Additionally, slight variations in the obtained measurements or the calibration process can lead to inaccuracies in the generated three-dimensional radiographic information.

Methods have been developed to help overcome the difficulties present in obtaining and maintaining the radiographic geometry of a system during the process of obtaining the radiographic images. One conventional method employed when unstable geometry is involved is optical tracking. With optical tracking, the system utilizes multiple visible light cameras configured in different positions relative to the subject together with markers attached to the portions of the subject that are unstable. The multiple cameras track movement of the subject by detecting the position of the markers. However, these systems have the disadvantage of requiring multiple visible light cameras configured in multiple directions relative to the subject as well as requiring the use of markers attached to the subject.

Self-calibrating systems for determining the radiographic geometry have also been developed for use in tomosynthesis. These systems typically involve positioning a radiopaque fiducial in a fixed position relative to the subject. Using the position of the fiducial in the radiographic images, the radiographic geometry of the system can be determined. The system then produces tomographic images of the subject using the calculated geometry. These types of systems also have disadvantages in that the use of radiopaque fiducials is required and the radiopaque fiducials can obscure portions of the radiographic image. Additionally, detecting the fiducials in the resulting radiographic images only provides relative geometry. Actual measurements are still required in order to determine the exact geometry of the system.

SUMMARY OF THE INVENTION

The present invention addresses the foregoing problems by recovering the radiographic geometry of a system using visible light images taken in correspondence to radiographic images. In particular, the present invention recovers the radiographic geometry of a system by applying stereoscopic analysis to visible light images taken in correspondence to radiographic images. Three-dimensional radiographic information is then generated and manipulated using the recovered radiographic geometry.

Accordingly, one aspect of the present invention concerns processing up to a plurality of radiographic images of a subject. At least two visible light images of the subject are captured, where two or more of the visible light images are in correspondence to at least one radiographic image. The at least two visible light images are captured by one or more visible light cameras, each visible light camera in a known geometric relation to the radiographic source. Radiographic geometry of each radiographic image relative to radiographic source and the subject is calculated through stereoscopic analysis of the at least two visible light images and through reference to the known geometric relation between the one or more visible light cameras and the radiographic source. Three-dimensional radiographic information on the subject is generated by processing the up to a plurality of radiographic images based on the calculated radiographic geometry.

By virtue of the foregoing, the present invention generates three-dimensional radiographic information on a subject even in situations where the geometry of the system is unstable or unknown. By calculating the radiographic geometry using visible light images, the invention has the advantage of not requiring error-prone measurement and calibration of the entire system when obtaining the radiographic images. Additionally, since the geometry is recovered by applying stereoscopic analysis to visible light images, the invention does not require the use of markers or radiopaque fiducials which can obscure data and require additional set-up and installment procedures and measurements. Finally, by obtaining visible light images in correspondence with radiographic images, the visible surface structure of a subject can be reconstructed and registered with the corresponding internal structure of the subject shown in the radiographic images, so as to facilitate procedures such as reconstructive plastic surgery.

This brief summary has been provided so that the nature of the invention may be understood quickly. A more complete understanding of the invention can be obtained by reference to the detailed description of the preferred embodiment thereof in connection with the attached drawings.

DETAILED DESCRIPTION OF THE INVENTION

Figure 1:
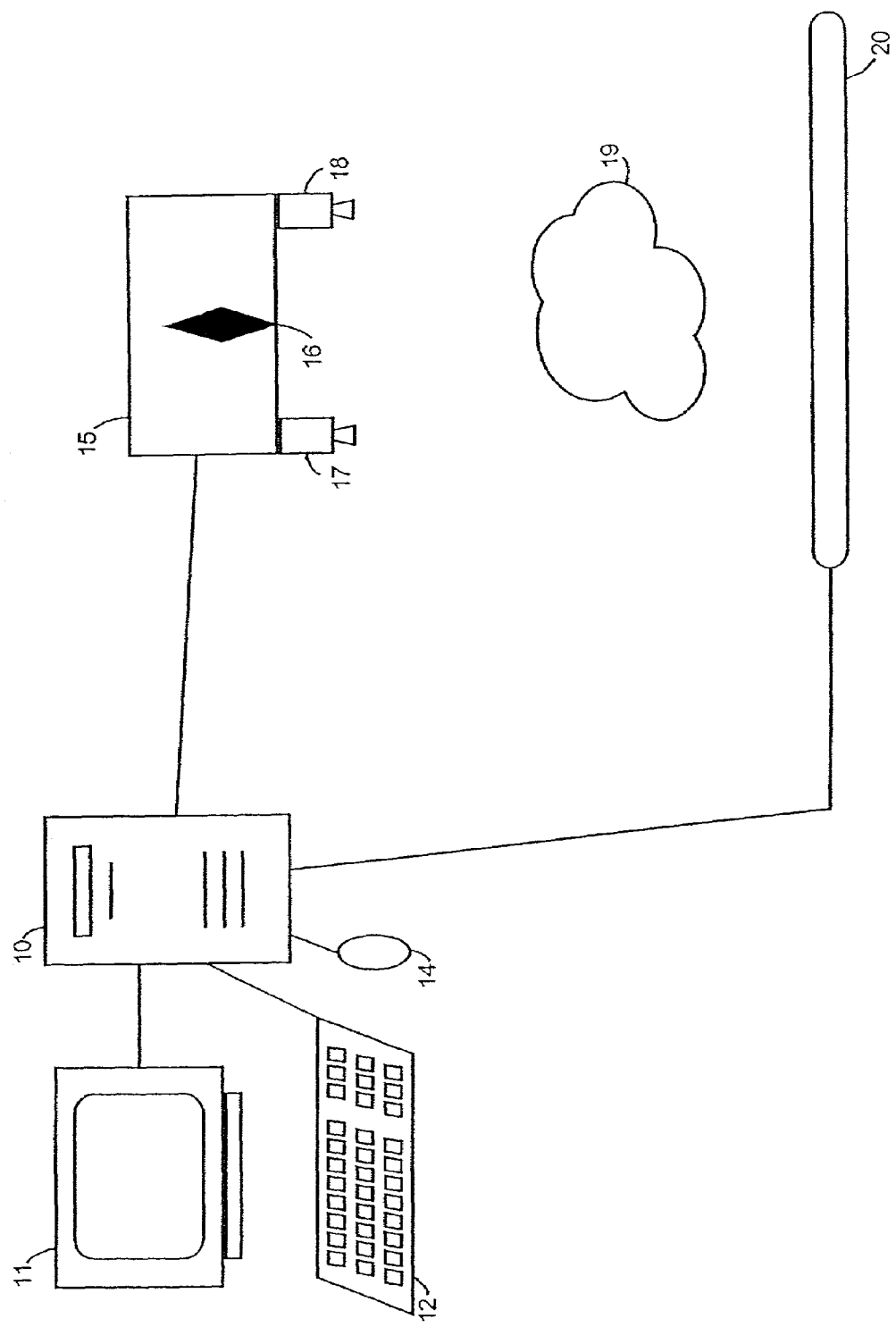
FIG. 1 is a depiction of a radiographic system in which the invention may be practiced.

FIG. 1 depicts a radiographic system for obtaining radiographic images of a subject in which the invention may be utilized. Computing device 10 controls the operation of the radiographic system and performs processing according to the invention, which is described in more detail below. Computing device 10 may be a personal computer, a workstation or some other type of general or special purpose computing system. Keyboard 12 and pointing device 14 are input devices for receiving and transmitting user input to computing device 10. Input devices for computing system 10 are not limited to keyboard 12 and pointing device 14 and may include other possible input devices such as a touch-screen system or a light-pen device. Display 11 displays user input, user interfaces generated by computing device 10, and processing results generated by computing device 10. Display 11 may be, but is not limited to, a CRT monitor or a flat-panel display. In addition, a printing device (not shown) such as a laser printer may be used to output processing results of computing device 10.

Imaging head 15 includes a radiographic source such as x-ray source 16 that irradiates subject 19 during a process of obtaining radiographic images of subject 19. The movement and control of imaging head 15 may be controlled manually by a user or alternatively may be controlled by a software module or user input through computing device 10. Sensor 20 is a radiographic sensor that detects x-rays emitted by x-ray source 16. When subject 19 is irradiated by x-ray source 16, the locations of the x-rays on sensor 20 are detected and used to form radiographic images of subject 19.

Imaging head 15 also includes cameras 17 and 18. Cameras 17 and 18 are visible light cameras, and are preferably digital cameras that capture and store a visible light image in a digital format. Cameras 17 and 18 are in known or easily determined positions relative to x-ray source 16 and may be fixed in those relative positions or movable by a user. Alternatively, cameras 17 and 18 may be physically separate from imaging head 15 as long as the relative positions of cameras 17 and 18 and x-ray source 16 are known or ascertainable. Although two cameras are shown, the effect of the invention can also be obtained with one camera that captures multiple images in stereoscopic relation.

Figure 2:
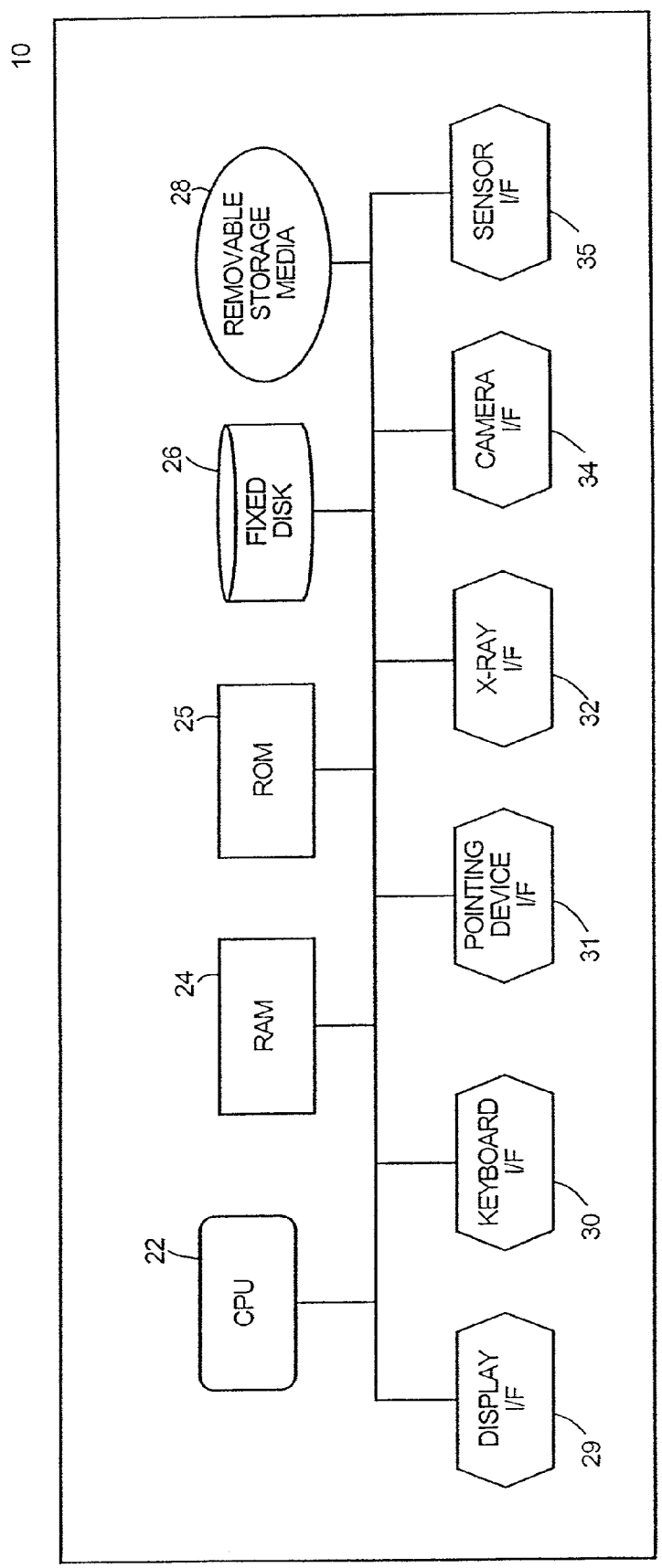
FIG. 2 is a block diagram depicting the internal architecture of a computing device used in the invention.

FIG. 2 is a block diagram illustrating the internal architecture of computing device 10. Central processing unit (CPU) 22 is a microprocessor that performs control functions for peripherals attached to computing device 10 as well as executing instructions of software modules being executed on computing device 10. CPU 22 is interfaced to bus 21 which provides for communication and transfer of data between components of computing device 10. Random access memory (RAM) 24 is a run-time memory in which instruction sequences are loaded from fixed disk 26, or some other form of computer-readable storage media, by CPU 22 prior to being executed. Additionally, RAM 24 provides memory space for CPU 22 to execute instruction sequences and perform computations.

Read only memory (ROM) 25 stores invariant instruction sequences, such as startup instruction sequences for CPU 22 and basic input/output operating system (BIOS) sequences for controlling peripheral devices connected to computing device 10. Fixed disk 26 is a computer-readable storage medium that stores software modules executed on computing device 20, which will be described in more detail below, and provides storage space for data received and generated by computing device 10. Removable storage media interface 28 provides access to one or more forms of removable computer-readable storage media. Possible types of removable storage media include floppy disks, CD-ROMs, Compacflash, etc.

As can be seen in FIG. 2, computing device 10 also contains multiple interfaces for connecting and communicating with peripheral devices. Display interface 29 connects display 11 with computing device 10 and provides means for data and user interfaces to be displayed on display 11. Keyboard interface 30 and pointing device interface 31 provide means for connecting and receiving user input from a keyboard or a pointing device such as a mouse. X-ray interface 32 provides means for connecting and controlling imaging head 15 and x-ray source 16. Camera interface 34 provides means for connecting and controlling cameras 17 and 18 as well as receiving digital image data captured by cameras 17 and 18. Sensor interface 35 provides means for connecting sensor 20 and for receiving radiographic image data captured by sensor 20. The peripheral devices listed above are provided as examples of possible peripheral devices connectable to computing device 10. It is to be understood, however, that other peripheral devices in addition to those listed above may be connected to computing device 10.

Figure 3:
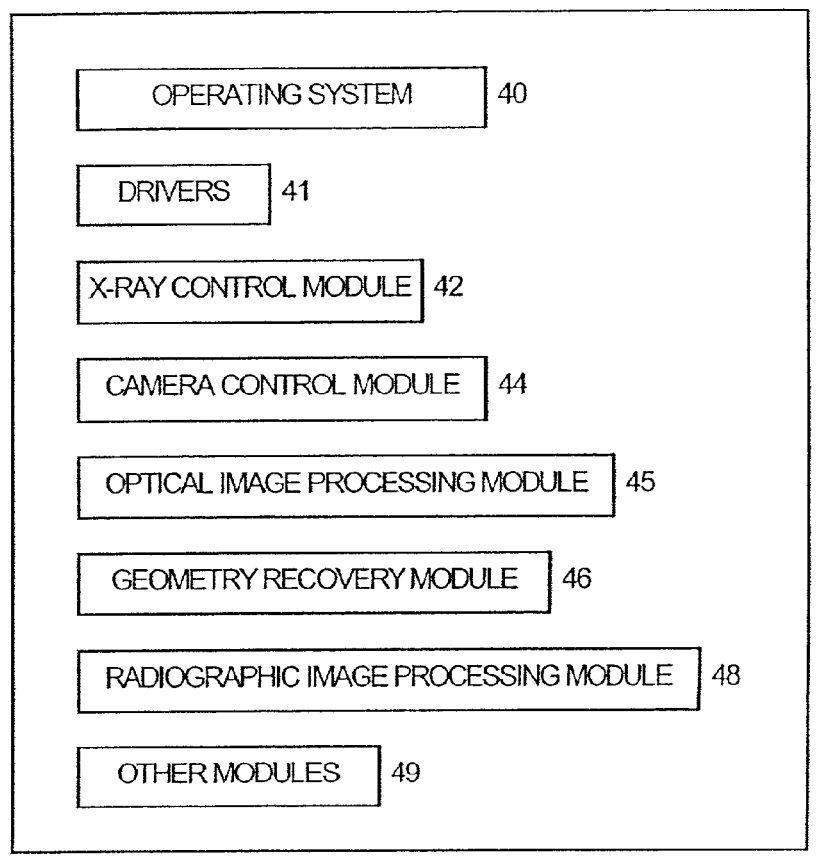
FIG. 3 is a block diagram depicting the contents of a computer-readable medium used in the invention.

FIG. 3 is a block diagram depicting the contents of fixed disk 26. Fixed disk 26 stores software modules that include operating system (OS) 40, drivers 41, x-ray control module 42, camera control module 44, optical image processing module 45, geometry recovery module 46, radiographic image processing module 48 and other modules 49. OS 40 may be a windowing operating system, such as Windows 2000, or may be a UNIX/Linux based operating system. OS 40 manages applications running on computing device 10 as well as the various components that make up computing device 10. Drivers 41 provides software drivers to facilitate communication between applications running on computing device 10 and peripherals attached to computing device 10.

X-ray control module 42 is software for controlling imaging head 15 and x-ray source 16. Possible control functions performed by x-ray control module 42 may include, but are not limited to, turning x-ray source 16 on and off and positioning imaging head 15 relative to subject 19. X-ray control module 42 also controls sensor 20 and stores radiographic image data captured by sensor 20 on a storage medium such as fixed disk 26. Camera control module 44 is software for controlling the operation of cameras 17 and 18 and for retrieving and storing visible light image data acquired by cameras 17 and 18.

Optical image processing module 45 and geometry recovery module 46 are software for performing image processing and stereoscopic analysis of visible light images. Optical image processing module 45 is software for processing and manipulating visible light image data acquired by cameras 17 and 18. Functions performed by optical image processing module 45 include, but are not limited to, color component separation, image cropping, segmentation, thresholding, depth determination, surface topography construction and calculation of correlation functions. Through known applications of these techniques, optical image processing module 45 identifies one or more reference points on a subject captured in multiple visible light images and determines matching points within the multiple visible light images that correspond to the one or more reference points. Using the matching points located by optical image processing module 45, geometry recovery module 46 calculates the system geometry of the radiographic system. The process of determining the matching points and the calculation of the system geometry using those points will be described in more detail below.

Radiographic image processing module 48 is software for processing the radiographic image data acquired by sensor 20 when subject 19 is irradiated by x-ray source 16. In addition to generating two-dimensional radiographic images, radiographic image processing module 48 may be configured to generate three-dimensional radiographic information using the system geometry recovered by geometry recovery module 46. Possible three-dimensional radiographic information includes, but is not limited to, stereoscopic x-ray imaging, digital tomosynthesis, and volume reconstruction.

Other modules 49 includes other software modules that may be utilized by a user operating computing system 10. For example, software modules may be included for registering the surface topography of subject 19 obtained from visible light images with reconstructed three-dimensional radiographic information.

The contents of fixed disk 26 are not limited to those modules described above. In addition to the modules described above, visible light image data, radiographic image data and other types of data may also be stored on fixed disk 26. Additionally, one or more of the modules described above may be stored on and executed from a different computer-readable storage medium, such as a floppy disk or CD-ROM, or from a local or wide area network, intranet or internet.

Figure 4:
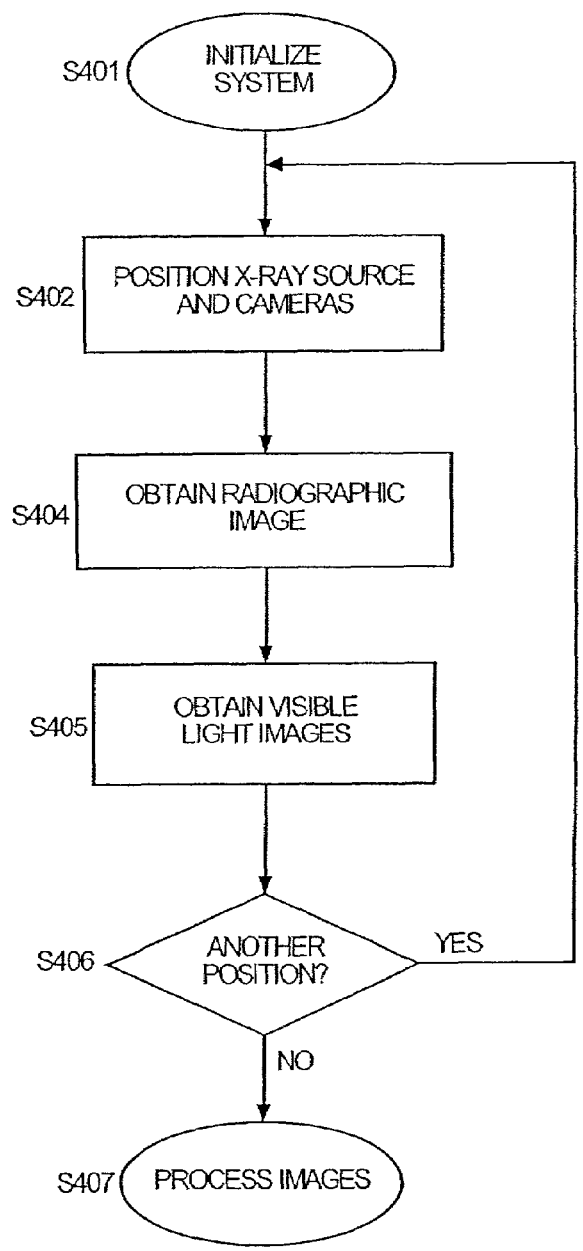
FIG. 4 is a flowchart for explaining the operation of the radiographic system.

FIG. 4 is a flowchart for explaining the operation of the radiographic system described above as performed by the software modules described in reference to FIG. 3. Briefly, according to FIG. 4, imaging head 15 is positioned with respect to subject 19 and multiple radiographic and visible light images of subject 19 are acquired using x-ray source 16, sensor 20 and cameras 17 and 18. The acquired images are thereafter processed, as described below with reference to FIG. 6, to obtain three-dimensional radiographic information. Of course, all images need not be obtained before processing of FIG. 6 begins, although this is preferred.

In more detail, in step S401, the radiographic system is initialized. Computing device 10 is turned on and software modules are loaded from fixed disk 26 or other storage media where software modules may be stored. The loaded software modules may include OS 40, drivers 41, x-ray control module 42 and camera control module 44. In addition, imaging head 15, x-ray source 16, sensor 20 and cameras 17 and 18 are connected to computing device 10 and turned on. Finally, subject 19 is positioned between imaging head 15 and sensor 20.

Subject 19 may be a human being or an animal when the radiographic system is used for medical purposes. Alternatively, subject 19 might be a mechanical part or structure when the radiographic system is used for industrial analysis purposes.

In step S402, imaging head 15 together with x-ray source 16 and cameras 17 and 18 are positioned. Imaging head 15 is positioned relative to subject 19 in order to acquire a radiographic image of subject 19 using x-ray source 16 and sensor 20. As mentioned above, cameras 17 and 18 are in known or ascertainable positions relative to x-ray source 16. The positions of cameras 17 and 18 may be fixed relative to x-ray source 16, or the positions may be adjustable by a user prior to beginning acquisition of radiographic images of subject 19.

Figure 5:
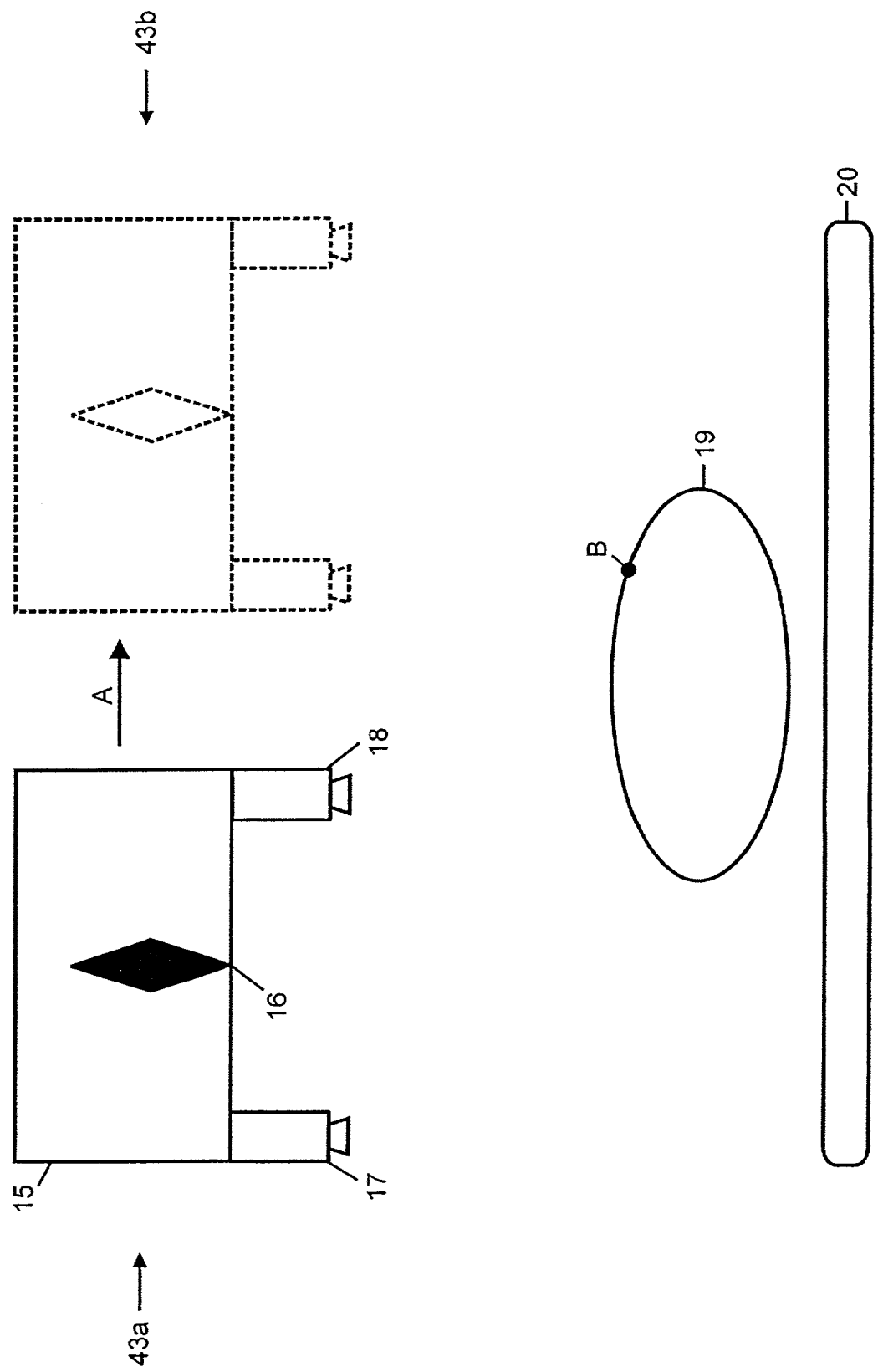
FIG. 5 is a depiction explaining the positioning of the radiographic system according to a first embodiment of the invention.

FIG. 5 depicts representative positioning of the radiographic system according to the first embodiment of the invention. In order to generate three-dimensional radiographic information from two-dimensional radiographic images, the two-dimensional radiographic images are acquired from different positions relative to subject 19. In this embodiment, imaging head 15, together with x-ray source 16 and cameras 17 and 18, are moved along a direction indicated by arrow A while irradiating subject 19 from different positions along arrow A. For example, from a first position at 43a to a second position (shown in phantom lines) at 43b. Arrow A is a direction parallel to sensor 20, thereby keeping the distance between x-ray source 16, and therefore also cameras 17 and 18, and sensor 20 constant for each of the different positions. Additionally, in this embodiment subject 19 is in a fixed position relative to sensor 20 and therefore the only element changing positions during the acquisition of radiographic images is imaging head 15. Accordingly, in step S402 imaging head 15 is positioned somewhere along arrow A.

As mentioned above, control of the movement of imaging head 15 may be provided from different sources. For example, a user might manually position imaging head 15 along arrow A or select desired positions using a user interface displayed on display 11 by computing device 10. Alternatively, x-ray control module 42 might be programmed to move imaging head 15 through a series of predetermined positions along arrow A.

In step S404, motion of imaging head 15 is stopped, and a radiographic image is acquired by sensor 20 for the present position of imaging head 15. The radiographic image is acquired by x-ray source 16 irradiating subject 19 and sensor 20 detecting the locations where x-rays reach sensor 20. The radiographic image for the position of x-ray source 16 is retrieved from sensor 20 and stored by computing device 10 on fixed disk 26 or some other type of computer-readable storage medium.

In step S405, cameras 17 and 18 each obtain a visible light image of subject 19 from the current position of imaging head 15. The visible light images from each of cameras 17 and 18 are retrieved and stored by computing device 10 on fixed disk 26 or some other computer-readable storage medium. The visible light images may be obtained by cameras 17 and 18 before, during or after the radiographic image has been obtained for that particular position. Both the radiographic image and the visible light images are obtained at the same position of imaging head 15.

In step S406, it is determined whether more radiographic images are desired. If more radiographic images are desired, imaging head 15 is moved to a new position along arrow A and steps S402 through S405 are repeated. Steps S402 through S405 are repeated until all radiographic images have been obtained. Once all radiographic images have been obtained, the process proceeds to step S407, in which the radiographic images and the visible light images are processed. The processing of the images will be explained in more detail below with reference to FIG. 6.

As described above, computing device 10 retrieves and stores the radiographic images and the visible light images as they are acquired by sensor 20 and cameras 17 and 18, respectively. Alternatives to this procedure might include sensor 20 (or imaging head 15) storing the radiographic images internally and cameras 17 and 18 storing the visible light images internally until the process reaches step S407. At this point, the images could be uploaded to computing device 10 via a direct connection or a network connection, or transferred to computing device 10 using a removable storage medium. Other alternatives might include capturing the images using film and then scanning the film into computing device 10 using a scanning device and then processing the images scanned from the film according to the invention. Once the images have been received and stored on computing device 10, the processing of step S407 proceeds.

According to the description provided above, cameras 17 and 18 obtain visible light images at each of the positions of imaging head 15 in which subject 19 is irradiated and a radiographic image is obtained. However, if the relative positions of imaging head 15 along arrow A at which radiographic images are obtained are known with good accuracy, cameras 17 and 18 need only obtain visible light images at one of the known positions. The system geometry can be recovered for that particular position using the visible light images, as described below, and the system geometry for the remaining positions can be determined using the known relationship between the known position imaging head 15 and the other positions for which the geometry is sought.

Figure 6:
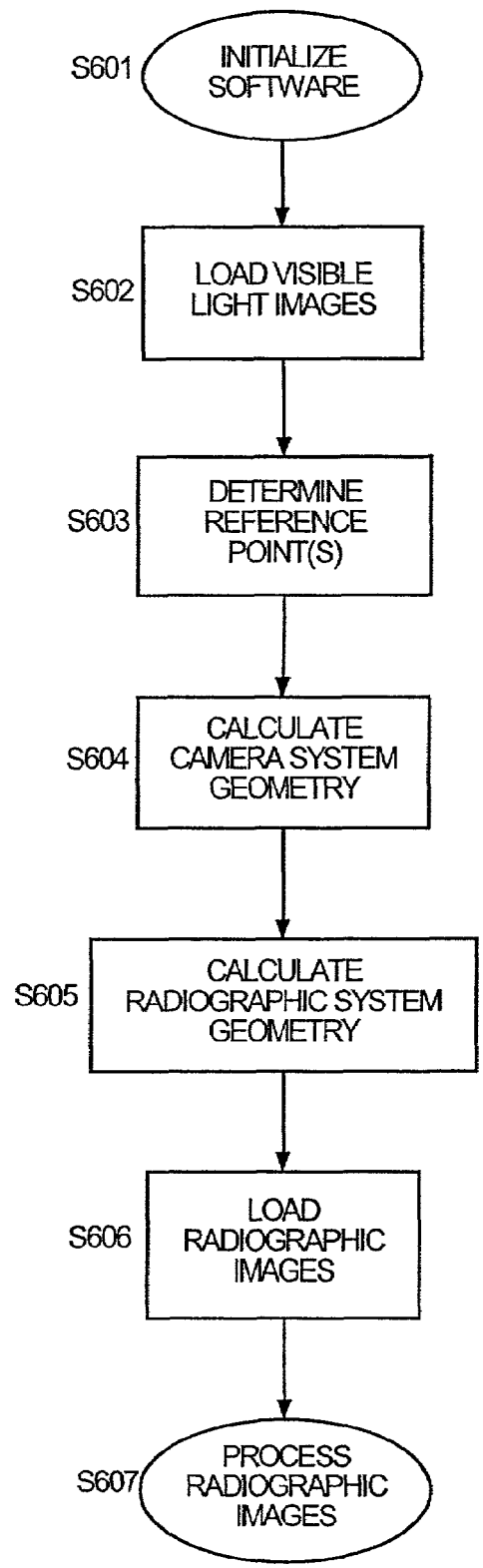
FIG. 6 is a flowchart for explaining the processing of image data.

FIG. 6 is a flowchart for explaining the processing of the visible light images to obtain the system geometry and the processing of the radiographic images to generate three-dimensional radiographic information as executed by the software modules described above with reference to FIG. 3. Briefly, according to FIG. 6, the visible light images are processed and stereoscopic analysis is performed to determine the system geometry with respect to the visible light cameras. Using the system geometry with respect to the visible light cameras, the radiographic system geometry is recovered. Finally, the radiographic images are processed using the recovered system geometry and three-dimensional radiographic information is generated.

In more detail, in step S601, software modules in computing device 10 are loaded and initialized. The loaded software modules include optical image processing module 45, geometry recovery module 46 and radiographic image processing module 48. The software modules may be initialized when computing device 10 is powered on, when the radiographic system is set up, or after all the images of subject 19 have been acquired.

In step S602, optical image processing module 45 loads the visible light images acquired by cameras 17 and 18 into RAM 24 for further processing. For purposes of this description, the processing of a set of visible light images acquired from a single position of x-ray source 16 will be described below. It is to be understood, however, that the system geometry from any position of x-ray source 16 may be recovered using the same process with visible light images acquired from the position of interest.

In the first embodiment, subject 19 and sensor 20 are fixed with respect to each other. Only imaging head 15, together with x-ray source 16 and cameras 17 and 18, move with respect to subject 19. In this configuration, it is sufficient to identify a single reference point on subject 19 and locate that point within the acquired visible light images in order to recover the system geometry. The system geometry in this embodiment includes the relative positions of x-ray source 16, sensor 20 and the reference point on subject 19.

In step S603, a reference point on subject 19, together with matching points corresponding to the reference point in each of the visible light images acquired by each of cameras 17 and 18, are obtained using known image processing techniques. The reference point is a point on the surface of subject 19 that appears in both the visible light image acquired by camera 17 and the visible light image acquired by camera 18. In FIG. 5, the reference point on subject 19 is depicted as point B.

A variety of known and yet-to-be-developed matching techniques may be used for locating the reference point in the visible light images. Possible techniques include feature matching and correlation matching. With feature matching, a point is located in a first visible light image and then a matching point is located in a second visible light image using segmentation and thresholding methods. For example, the image data may be separated into color components with a subset of the visible light image data containing only the red component of the visible light image. The brightest portion of the red component of the first visible light image is identified and the matching portion of the red component of the second visible light image is then located using segmentation and thresholding. This is only one example of feature matching that may be used in the present invention. Any of a number of other techniques for feature matching may also be used to locate the reference point in the visible light images.

Another matching technique that may be employed is correlation matching. With correlation matching, a reference point in a first visible light image is selected and then a correlation function is calculated with respect to the second visible light image. The correlation function then produces the best match in the second visible light image for the selected reference point in the first visible light image. The reference point selected in the first visible light image may be selected using any of a number of methods for selecting a single point within a visible light image. For example, the center point of the image data may be selected. Alternatively, a point in the center of the highest concentration of a particular color component of the image data may be selected.

In step S604, the geometry of the radiographic system with respect to cameras 17 and 18 is calculated. Using the reference point and the corresponding matching points in the visible light images identified in step S603, the relative positions of cameras 17 and 18 and reference point B on subject 19 are determined. Using this information, the relative positions of x-ray source 16, sensor 20 and subject 19 are then calculated.

Figure 7:
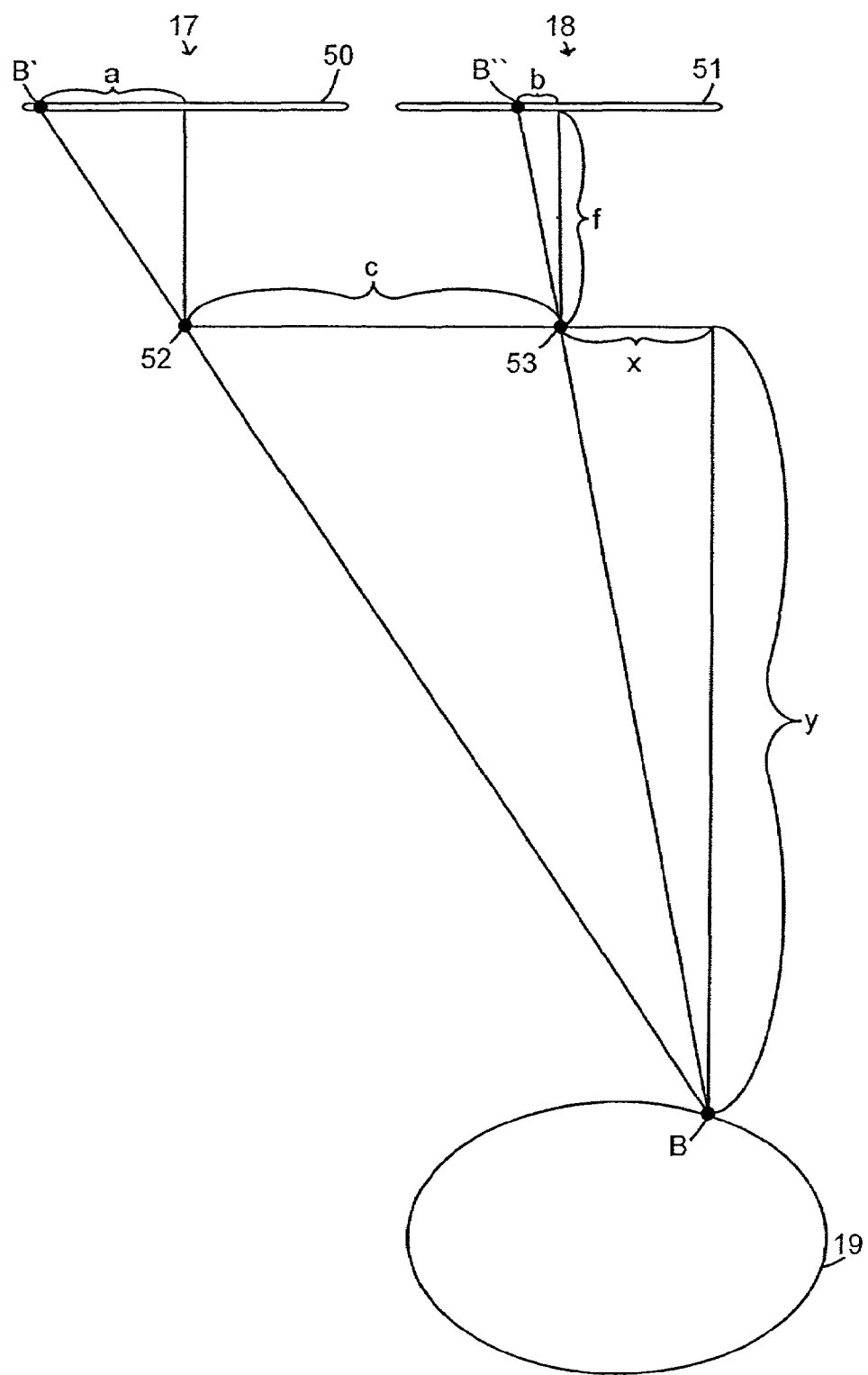
FIG. 7 is a representative example for determining the geometry of the system with respect to the visible light cameras in the first embodiment.

FIG. 7 is a representative example for determining the geometry of the system with respect to subject 19 and cameras 17 and 18. For purposes of explanation, some of the elements of the radiographic system have been excluded from FIG. 7. Cameras 17 and 18 are depicted in FIG. 7 as optical sensors 50 and 51 and focal points 52 and 53, respectively. Segment f represents the focal length between focal points 52 and 53 and optical sensors 50 and 51, respectively. In this description, cameras 17 and 18 are depicted as pinhole type cameras for purposes of explanation. It is understood, however, that other types of cameras may be employed as long the internal geometry of the type of camera used is taken into consideration when making the system geometry calculations.

Reference point B is the reference point on the surface of subject 19. Points B' and B" are matching points in the visible light images as captured by optical sensors 50 and 51 corresponding to reference point B. Points B' and B" are the matching points determined in step S603 as described above. Segment a and segment b represent the distances in the visible light images between the center of the visible light images and the location of points B' and B" in their respective visible light images. Segment c represents the distance between focal points 52 and 53 of cameras 17 and 18. The length of segment c is known based on the distance between the focal points of cameras 17 and 18 in the radiographic system.

Using the known segments depicted in FIG. 7, the distance of reference point B from focal points 52 and 53 is calculated using standard geometry. For example, the lengths of segments y and x are calculated using formulas (1) and (2), respectively.

$$y = f*c/(a-b) \quad (1)$$

$$x = b*y/f \quad (2)$$

In this manner, all segment lengths depicted in FIG. 7 are determined. The calculations described above are one example of possible calculations for recovering the system geometry. It is understood, however, that other geometric techniques may be used to recover the system geometry.

In step S605, the system geometry of the radiographic system with respect to x-ray source 16 is determined. Using the positions of cameras 17 and 18 determined in step S604, the relative position of x-ray source 16 is determined based on the known relative positions of x-ray source 16 and cameras 17 and 18.

Figure 8:
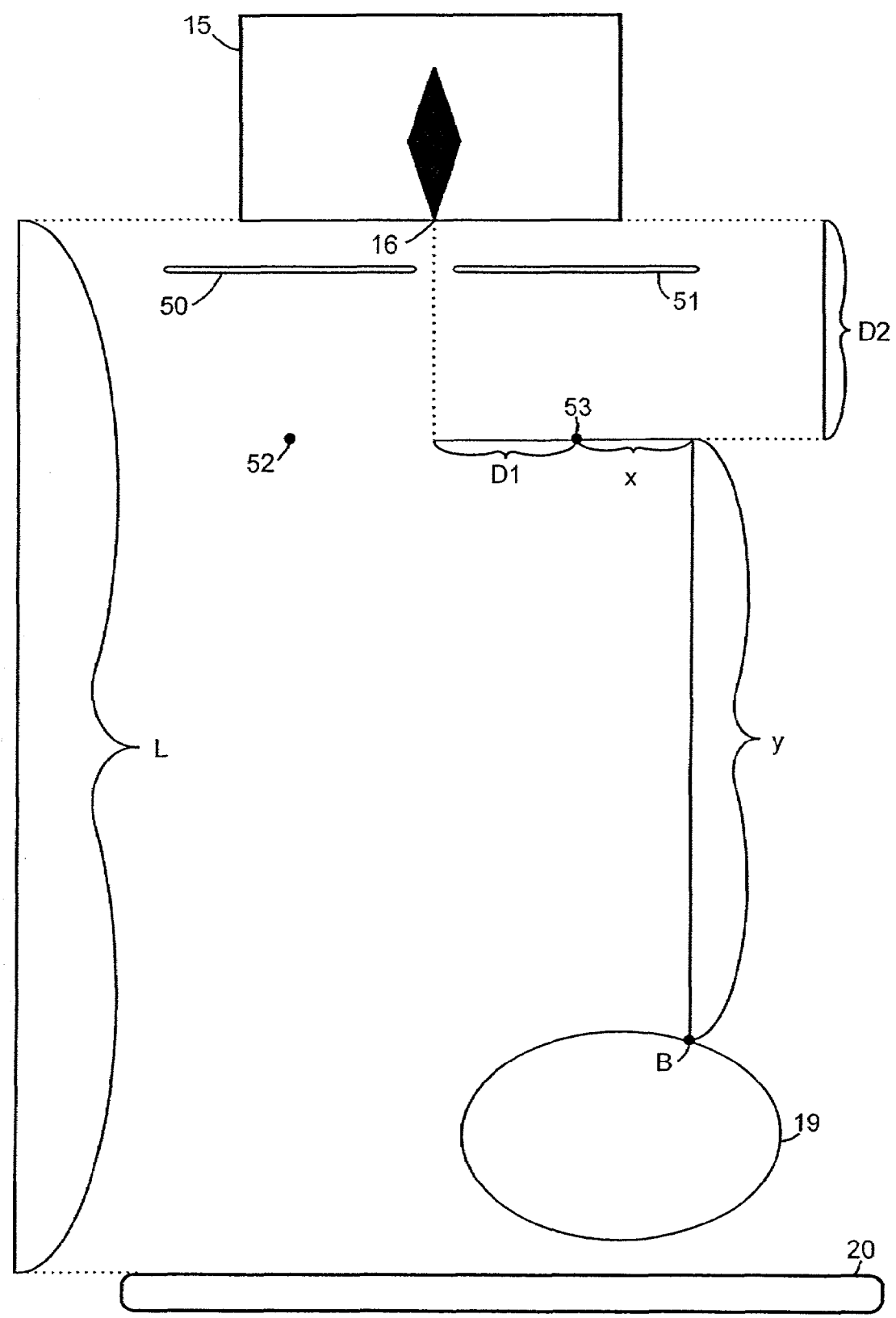
FIG. 8 is a representative example for determining the system geometry of the radiographic system in the first embodiment.

FIG. 8 is a representative example for determining the system geometry of the radiographic system with respect to x-ray source 16, sensor 20 and subject 19. Segments x and y represent the position of focal point 53 of camera 18 with respect to reference point B of subject 19. The lengths of segments x and y were determined in step S604 in the manner described above with reference to FIG. 7. Segment L is the distance between x-ray source 16 and sensor 20, which is known.

As mentioned above, the relative positions of cameras 17 and 18 and x-ray source 16 are known or ascertainable. Accordingly, the relative position of focal point 53 of camera 18 and x-ray source 16 is known or ascertainable as well. Segments D1 and D2 represent the position of x-ray source 16 with respect to focal point 53. By combining segments D1 and D2 with segments x and y, respectively, the position of x-ray source 16 with respect to reference point B of subject 19 is determined.

In the event that the length of segment L is unknown, the length can be recovered in the manner described above with respect to FIGS. 7 and 8 using visible light images captured by cameras 17 and 18. Using the previously described method for identifying a reference point B on subject 19, a reference point is identified on sensor 20 and corresponding matching points within the captured visible light images are located. Using the geometric calculations described with respect to FIG. 7, the relative positions of sensor 20 and focal points 52 and 53 are recovered. The relative position of sensor 20 to x-ray source 16 is then obtained in the manner described with reference to FIG. 8.

In the manner described above with respect to FIGS. 7 and 8, the relative positions of x-ray source 16, sensor 20 and subject 19, which makes up the system geometry of the radiographic system, are recovered. Once the system geometry has been recovered in step S605, the radiographic images captured by sensor 20 are loaded into RAM 24 for further processing in step S606. Alternatively, the radiographic images could be loaded into RAM 24 before or at the same time as loading the visible light images. In step S607, radiographic image processing module 48 processes the radiographic images using the recovered system geometry to generate three-dimensional radiographic information.

Different forms of three-dimensional radiographic information can be generated by the invention using known and yet-to-be-developed techniques. Examples include: stereoscopic x-ray imaging, digital tomosynthesis, volume reconstruction, cone-beam tomography and zoom factors. These examples are explained in more detail below.

With respect to stereoscopic x-ray imaging, a pair of radiographic images are acquired of a subject and viewed as a stereoscopic x-ray image pair. When the stereoscopic x-ray image pair is viewed with the proper equipment, the two-dimensional radiographic images of the subject appear to be three-dimensional.

Using known and yet-to-be-developed stereoscopic techniques, the stereoscopic x-ray image pair is processed using the recovered geometry. Specifically, the relative positions of the x-ray source and the subject for each of the acquired radiographic images are used to correct for errors and distortions in the image pair and to improve depth perception. For example, the distance from the x-ray source to the subject is used for adjusting screen parallax and compensating for depth and size magnification. In the event that the radiographic images are captured from different angles relative to the subject, as will be described in additional embodiments discussed below, the angle of rotation and the axis of rotation are used to compensate for shearing and keystone distortions as well as depth plane curvature. In this manner, the recovered system geometry is utilized to generate an accurate stereoscopic x-ray image pair.

The invention may also be used to generate tomographic images of a subject produced through digital tomosynthesis. Tomosynthesis involves aligning a series of radiographic images of a subject that have been acquired from different positions relative to the subject and combining the aligned images to generate a tomographic image at a designated slice depth. To align the radiographic images, objects within a tomographic plane at a designated slice depth in the subject are aligned in the radiographic images. The relative positions of the x-ray source, subject and x-ray sensor are used to properly align and combine the radiographic images. Additionally, if the radiographic images are obtained at different angles relative to the subject, the angle of rotation and the location of the center of rotation for the radiographic images are also used to properly align and process the radiographic images.

With digital tomosynthesis, an unlimited number of slice depths within the subject can be designated to produce tomographic images. Each slice depth represents a tomographic plane within the subject. The location of the first tomographic plane is obtained from the location of the surface of the subject relative to the x-ray source. The distance from the x-ray source to the x-ray sensor provides the location of a final tomographic plane when the subject rests on the x-ray sensor. Using digital tomosynthesis techniques, the tomographic plane can be shifted an unlimited number of times between the first and last tomographic planes to obtain the tomographic images. The locations of the first and last tomographic planes are obtained from the recovered system geometry.

In addition to the two-dimensional tomographic images discussed above, a volume of the subject can be reconstructed with a series of generated tomographic images. By aligning and stacking the series of tomographic images of the subject, a three-dimensional volume of the subject is reconstructed.

As an alternative to combining two-dimensional tomographic images, the volume can be reconstructed using techniques such as cone-beam tomography. As in the two-dimensional tomography discussed above, the relative positions of the x-ray source, the subject and the x-ray sensor are used to obtain an accurate reconstruction in cone-beam tomography. Additionally, the angle of rotation and position of the center of rotation are also used for accurate reconstruction of the volume.

Once the volume of the subject has been reconstructed, surface information of the subject, obtained from the visible light images, can be registered with the internal volume obtained from the radiographic images. In this manner, a correlation between surface structure of the subject and the internal structure of the subject is obtained.

The invention is not limited to the forms of three-dimensional radiographic information described above. Other known and yet-to-be-developed forms of radiographic information may also be generated using the invention. For example, a magnification or zoom factor can be determined using the recovered system geometry. The zoom factor is used to compensate for magnification errors that result from objects within the subject that are closer to the x-ray source appearing larger in a radiographic image than those objects that are farther away from the x-ray source. Using the recovered relative positions of the x-ray source and the subject, together with the known or determined relative positions of objects within the subject, magnification errors are corrected in the radiographic images.

In the manner described above, the invention provides a method for obtaining the system geometry of a radiographic system using visible light images of the subject ordinarily without the need for placement of radiopaque fiducials on the subject or precise calibration of the entire radiographic system.

Figure 9:
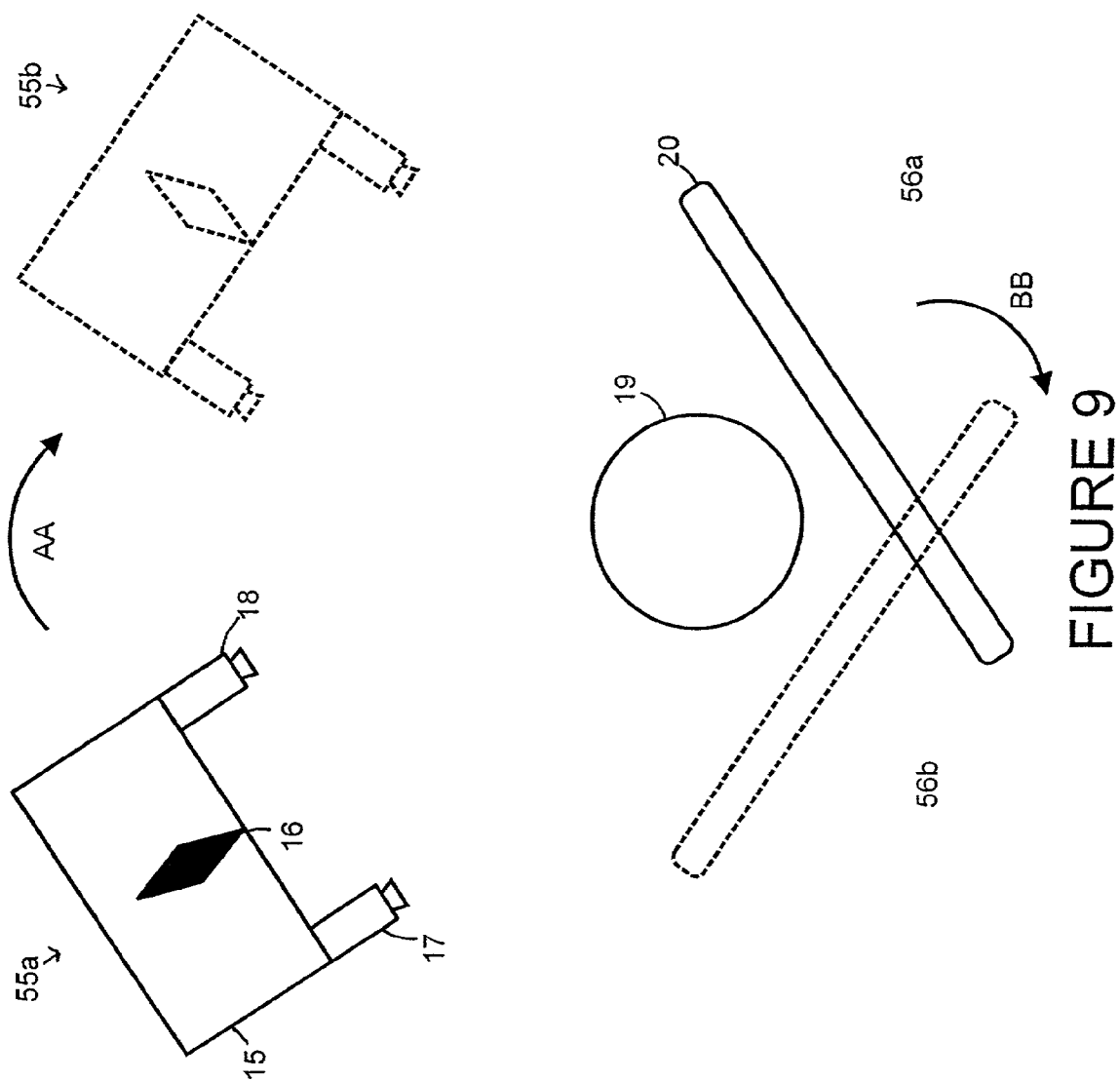
FIG. 9 is a depiction explaining the positioning of a radiographic system according to a second embodiment of the invention.

A second embodiment of the invention will now be described with reference to FIGS. 9 and 10. One way the second embodiment differs from the first is that the relative positions of subject 19 and sensor 20 are not fixed. FIG. 9 depicts representative positioning of imaging head 15 and sensor 20 relative to subject 19 according to the second embodiment. As in the first embodiment, the distance between imaging head 15 and sensor 20 is known and is constant during the process of acquiring radiographic images. In the second embodiment, as imaging head 15 moves through an arc indicated by arrow AA, from a first position at 55a to a second position (shown in phantom lines) at 55b, sensor 20 moves in an arc in the opposite direction indicated by arrow BB, from a first position at 56a to a second position (shown in phantom lines) at 56b. In this manner, imaging head 15 and sensor 20 are opposite each other and rotate around subject 19 during the process of acquiring radiographic images.

Radiographic and visible light images are acquired of subject 19 according to the process described above with reference to the flowchart depicted in FIG. 4. In addition to positioning imaging head 15, together with x-ray source 16 and cameras 17 and 18, in step S402, sensor 20 is also positioned in step S402 in the manner described above with reference to FIG. 9. Once the desired images have been acquired, the radiographic images and visible light images are processed according to the procedure described above with reference to FIG. 6. Variations in the procedure according to the second embodiment are described below.

Figure 10:
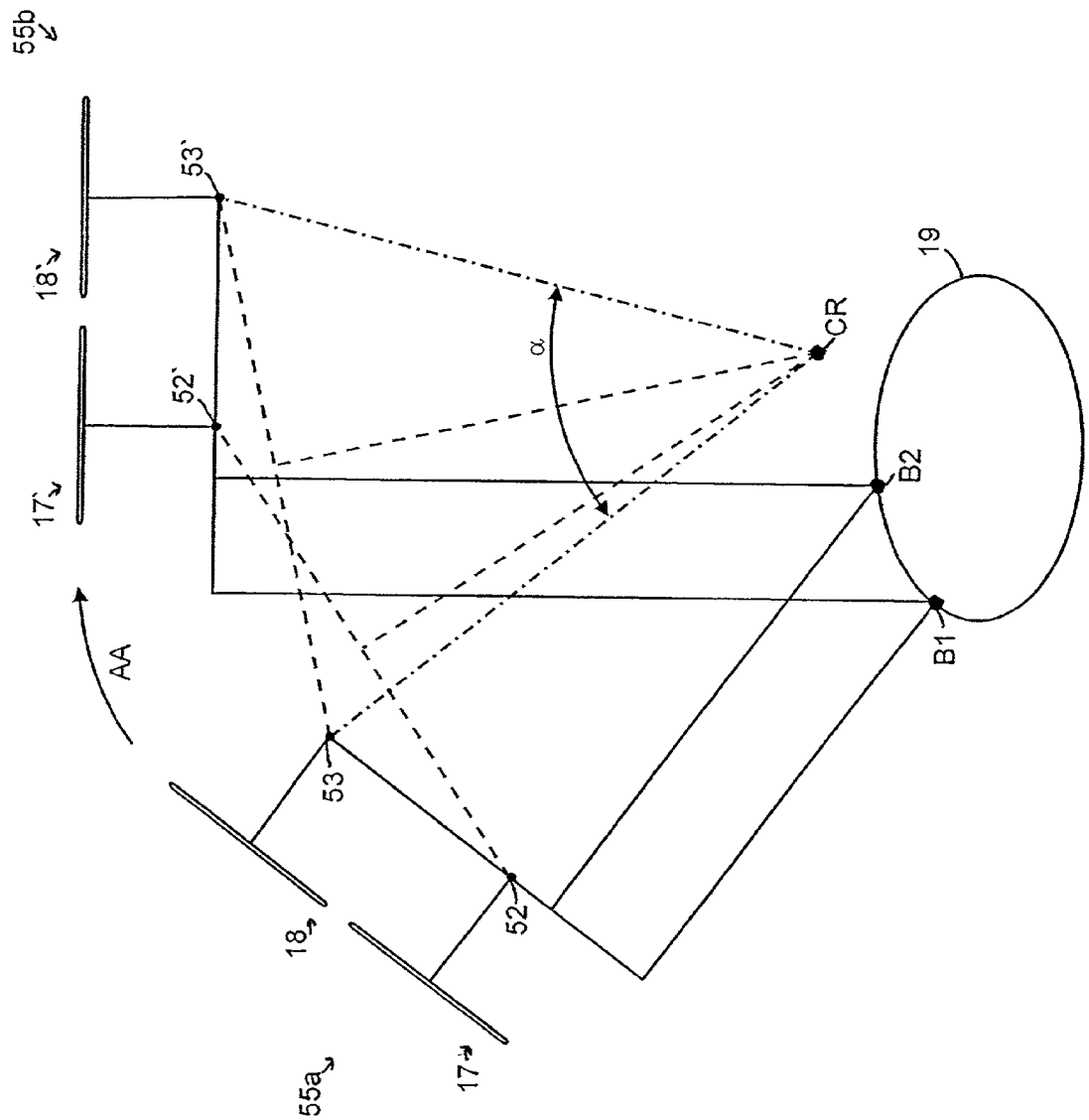
FIG. 10 is a representative example for determining the geometry of the system with respect to the visible light cameras in the second embodiment.

FIG. 10 is a representative example of the system geometry in the second embodiment of the invention with respect to cameras 17 and 18 and subject 19. For purposes of explanation, some of the elements of the radiographic system have been excluded from FIG. 10. In the second embodiment, imaging head 15 is moved through an arc indicated by arrow AA. Cameras 17 and 18, which move together with imaging head 15, also move from the first position 55a through the arc indicated by arrow AA to the second position 55b. Cameras 17' and 18' designate cameras 17 and 18 in the second position 55b along arrow AA. Similarly, focal points 52' and 53' designate focal points 52 and 53 of cameras 17 and 18 in the second position 55b along arrow AA.

For purposes of this explanation, the recovery of the system geometry of the radiographic system is explained with respect to imaging head 15 and sensor 20 obtaining radiographic images in two positions. It is to be understood, however, that the system geometry can be obtained for multiple other positions of x-ray source 16 and sensor 20 using the process described below.

Due to the rotational movement of both imaging head 15 and sensor 20 in the second embodiment, at least two references points, B1 and B2, on subject 19 are used to recover the system geometry. The system geometry in the second embodiment includes the relative positions of x-ray source 16, sensor 20 and subject 19, as well as the angle of rotation made by imaging head 15 and sensor 20 between positions in which radiographic images were acquired and the center of rotation CR. Using the techniques described above with respect to step S603 in FIG. 6, reference points B1 and B2 are identified on subject 19 and the matching points are identified in the visible light images acquired by cameras 17 and 18 in both positions 55a and 55b of imaging head 15 indicated in FIG. 10.

Once reference points B1 and B2 have been identified, the relative positions of cameras 17 and 18 with respect to reference points B1 and B2 are determined. Using the geometric analysis described in step S604 with respect to FIG. 7, the relative positions of cameras 17 and 18 with respect to each of reference points B1 and B2 are determined for each of the positions 55a and 55b of cameras 17 and 18. With these relative positions determined, a single coordinate system is established using reference points B1 and B2 as common landmarks.

In addition to the relative positions of cameras 17 and 18, the angle of rotation $\alpha$ along arrow AA also provides useful information about the system geometry. A center of rotation CR is determined by connecting the locations of each of focal points 52 and 53 with lines and extending perpendicular lines down from the center of the connecting lines. These connecting lines and perpendicular lines are represented in FIG. 10 as dashed lines. The intersection of the perpendicular lines provides the location of center of rotation CR. Using the center of rotation and the relative positions of either focal points 52 or 53 in the two positions 55a and 55b, the angle of rotation α is determined. The angle of rotation α is represented in FIG. 10 as the angle between the dot-and-dashed lines connecting focal points 53 and 53' with center of rotation CR.

In the manner described above, the geometry of the second embodiment of the invention is recovered with respect to the relative positions of subject 19 and cameras 17 and 18. Using the procedure described above in step S605 with respect to FIG. 8, the relative position of x-ray source 16 with respect to subject 19 is derived from the recovered geometry of the relative positions of subject 19 and cameras 17 and 18. The relative positions of x-ray source 16 and subject 19 together with the known distance between x-ray source 16 and sensor 20 and the determined angle of rotation α, with the center of rotation CR, make up the system geometry of the radiographic system in the second embodiment. With the system geometry, the radiographic images acquired by x-ray source 16 and sensor 20 are processed and three-dimensional radiographic information generated in the manner described above with respect to step S607 of FIG. 6.

The second embodiment was described above as recovering the system geometry of the radiographic system with respect two positions of imaging head 15. It is understood, however, that the system geometry can be recovered from multiple positions beyond the two described above using the same techniques. Also, if the relative positions of imaging head 15 are known accurately, only one position need be obtained through stereoscopic analysis.

Figure 11:
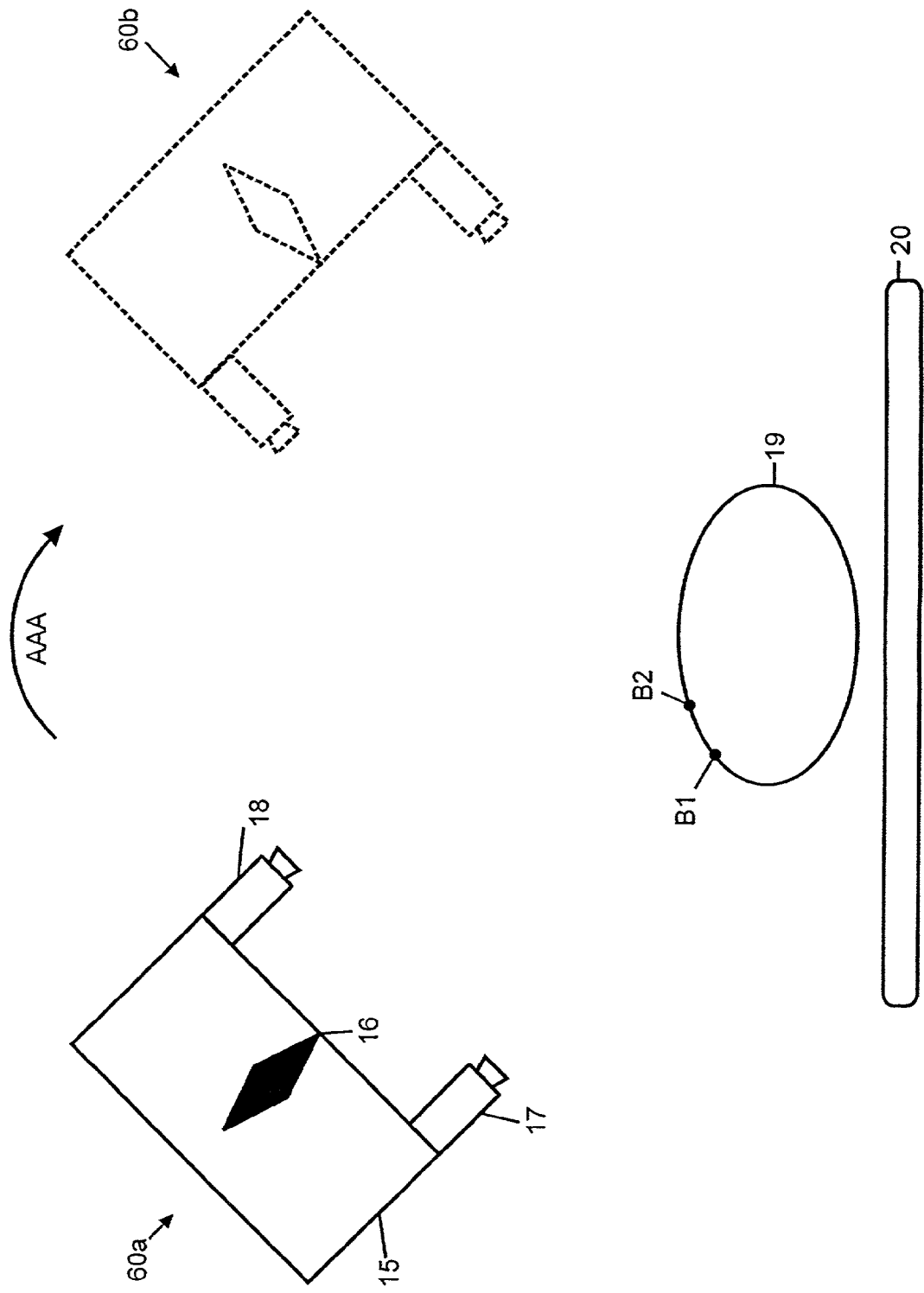
FIG. 11 is a depiction explaining the positioning of a radiographic system according to a third embodiment of the invention.

A third embodiment of the invention will now be described with reference to FIG. 11. FIG. 11 depicts representative positioning of components of a radiographic system according to the third embodiment of the invention. Like the first embodiment, sensor 20 remains in a fixed position relative to subject 19 during the process of acquiring radiographic images and visible light images. However, unlike the first embodiment, imaging head 15 does not move in a direction parallel to sensor 20. Rather, imaging head 15 is positioned along an arc indicated by arrow AAA, from a first position at 60a to a second position at 60b, as shown in FIG. 11. Accordingly, unlike the first two embodiments, the distance between imaging head 15 and sensor 20 is not constant during the process of acquiring radiographic images.

Radiographic images and visible light images are acquired in the third embodiment using the process described above with reference to the flowchart depicted in FIG. 4. The positioning of imaging head 15 in step S402 differs from the first embodiment, in that imaging head 15 is positioned along arc AAA, as described above with respect to FIG. 11. Once all the radiographic and visible light images have been acquired, processing proceeds to the procedure described above in reference to the flowchart depicted in FIG. 6. For purposes of explanation, not all of the steps depicted in FIG. 6 will be described with respect to the third embodiment.

As in the second embodiment, two reference points, B1 and B2, are identified on subject 19 to recover the system geometry of the radiographic system in the third embodiment. The system geometry includes the relative positions of x-ray source 16, subject 19 and sensor 20 as well as an angle of rotation α and a center of rotation CR. Using the techniques described above with respect to step S603 in FIG. 6, reference points B1 and B2 are identified on subject 19 and the matching points are identified in the visible light images acquired by cameras 17 and 18 in both positions 60a and 60b of imaging head 15 depicted in FIG. 11. The system geometry with respect to the relative positions of subject 19 and cameras 17 and 18 is recovered using the process described above with reference to FIGS. 7 and 10. Additionally, an angle of rotation α and a center of rotation CR are also obtained as described above with respect to FIG. 10. The system geometry with respect to x-ray source 16 is then obtained in the manner described above in step S605 with respect to FIG. 8 for each of the positions 60a and 60b of imaging head 15 depicted in FIG. 11.

Unlike the first two embodiments, the distance between imaging head 15 and sensor 20 is not constant during the process of obtaining the radiographic images. Accordingly, the relative positions of imaging head 15 and sensor 20 must be obtained for each position of imaging head 15. As discussed above, the relative position of sensor 20 can be derived using the visible light images and identifying a reference point on sensor 20. Using the procedures discussed above with respect to determining the relative positions of subject 19 and x-ray source 16, the relative position of sensor 20 is obtained. However, in the process discussed above, the process of determining the relative position of sensor 20 only used a single reference point on sensor 20. In the third embodiment, since imaging head 15 partially rotates around the position of sensor 20, as depicted in FIG. 11, the plane in which sensor 20 lies with respect to x-ray source 16 is recovered in order to determine the relative positions of imaging head 15 and sensor 20. Accordingly, at least three reference points (not shown) are identified on sensor 20 in the manner described above with respect to step S603 in FIG. 6. The relative positions of the three reference points with respect to the other elements in the radiographic system are determined in the manner described above with respect to FIGS. 7 and 8. The three reference points are used to define the plane in which sensor 20 lies with respect to imaging head 15.

In the manner described above, the system geometry of the third embodiment is recovered. Specifically, the relative positions of x-ray source 16, subject 19 and sensor 20, as well as the angle of rotation α and the center of rotation CR are recovered. With the recovered geometry, the radiographic images acquired by x-ray source 16 and sensor 20 are processed in the manner described above with respect to step S607 in FIG. 6 to generate three-dimensional radiographic information.

The embodiments described above include descriptions of particular geometric analysis techniques. It is understood, however, that other geometric analysis techniques may be employed to recover the system geometry without departing from the scope of the invention.

Other embodiments of the invention include a radiographic system in which multiple x-ray sources are employed together with the visible light cameras. The system geometry of this type of radiographic system is recovered using the methods described above depending on which of the embodiments described above the positioning of the multiple x-ray sources corresponds.

The invention has been described with respect to particular illustrative embodiments. It is to be understood that the invention is not limited to the above-described embodiments and that various changes and modifications may be made by those skilled in the art without departing from the spirit and scope of the invention.

What is claimed is:

1. A method for processing one or more radiographic images of a subject, said method comprising the steps of:
   capturing at least two visible light images of the subject in correspondence to each radiographic image obtained from a radiographic source, the at least two visible light images being captured by one or more visible light cameras;
   obtaining a geometric relation between the radiographic source and the visible light cameras at the time when the visible light images were captured;
   calculating radiographic geometry of each radiographic image relative to the radiographic source and the subject, wherein said calculation step comprises stereoscopic analysis of the at least two visible light images to determine relative positioning of the visible light cameras and the subject, and calculation of the radiographic geometry from the relative positioning and from the geometric relation between the radiographic source and the visible light cameras; and
   generating three-dimensional radiographic information on the subject by processing the one or more radiographic images based on the radiographic geometry calculated in said calculating step.

2. A method according to claim 1, wherein the three-dimensional radiographic information includes stereoscopic x-ray images.

3. A method according to claim 1, wherein the three-dimensional radiographic information includes a tomosynthetic image at a designated slice depth into the subject.

4. A method according to claim 1, wherein the three-dimensional radiographic information includes a plurality of tomosynthetic images at a plurality of designated slice depths into the subject, and wherein the method further comprises the step of reconstructing a volume of the subject by combining the plurality of tomosynthetic images.

5. A method according to claim 1, further comprising the step of registering one or more of the visible light images with the three-dimensional radiographic information.

6. A method according to claim 1, wherein the known geometric relation between the visible light cameras and the radiographic source is adjustable.

7. A method according to claim 1, wherein the three-dimensional radiographic information includes a radiographic volume reconstructed from the plural radiographic images.

8. A method according to claim 1, further comprising the steps of:
   generating a surface topography of the subject by processing the visible light images; and
   registering the surface topography with the three-dimensional radiographic information.

9. A method according to claim 1, wherein at least two visible light cameras are used and wherein a first visible light camera is in a known geometric relation to the radiographic source and a geometric relation of a second visible light camera to the radiographic source is determined based on the known geometric relation of the first visible light camera to the radiographic source and a known geometric relation of the first visible light camera to the second visible light camera.

10. A method according to claim 1, wherein the three-dimensional radiographic information includes a zoom factor for correcting magnification error in at least one radiographic image.

11. Computer-executable process steps stored on a computer-readable medium, said computer-executable process steps for processing one or more of radiographic images of a subject, said computer-executable process steps executable to perform a method comprising the steps of:
    capturing at least two visible light images of the subject in correspondence to each radiographic image obtained from a radiographic source, the at least two visible light images being captured by one or more visible light cameras;
    obtaining a geometric relation between the radiographic source and the visible light cameras at the time when the visible light images were captured;
    calculating radiographic geometry of each radiographic image relative to the radiographic source and the subject, wherein said calculation step comprises stereoscopic analysis of the at least two visible light images to determine relative positioning of the visible light cameras and the subject, and calculation of the radiographic geometry from the relative positioning and from the geometric relation between the radiographic source and the visible light cameras; and
    generating three-dimensional radiographic information on the subject by processing the one or more radiographic images based on the radiographic geometry calculated in said calculating step.

12. Computer-executable process steps according to claim 11, wherein the three-dimensional radiographic information includes stereoscopic x-ray images.

13. Computer-executable process steps according to claim 11, wherein the tree-dimensional radiographic information includes a tomosynthetic image at a designated slice depth into the subject.

14. Computer-executable process steps according to claim 11, wherein the three-dimensional radiographic information includes a plurality of tomosynthetic images at a plurality of designated slice depths into the subject, and wherein the method performed by the process steps further comprises the step of reconstructing a volume of the subject by combining the plurality of tomosynthetic images.

15. Computer-executable process steps according to claim 11, further comprising the step of registering one or more of the visible light images with the three-dimensional radiographic information.

16. Computer-executable process steps according to claim 11, wherein the known geometric relation between the visible light cameras and the radiographic source is adjustable.

17. Computer-executable process steps according to claim 11, wherein the three-dimensional radiographic information includes a radiographic volume reconstructed from the plural radiographic images.

18. Computer-executable process steps according to claim 11, wherein the method performed by the process steps further comprises the steps of:
    generating a surface topography of the subject by processing the visible light images; and
    registering the surface topography with the three-dimensional radiographic information.

19. Computer-executable process steps according to claim 11, wherein at least two visible light cameras are used and wherein a first visible light camera is in a known geometric relation to the radiographic source and a geometric relation of a second visible light camera to the radiographic source is determined based on the known geometric relation of the first visible light camera to the radiographic source and a known geometric relation of the first visible light camera to the second visible light camera.

20. Computer-executable process steps according to claim 11, wherein the three-dimensional radiographic information includes a zoom factor for correcting magnification error in at least one radiographic image.

21. A computer-readable medium that stores computer-executable process steps, the computer-executable process steps for processing plural radiographic images of a subject, the computer-executable process steps executable to perform a method comprising the steps of:

capturing at least two visible light images of the subject in correspondence to each radiographic image obtained from a radiographic source, the at least two visible light images being captured by one or more visible light cameras;

obtaining a geometric relation between the radiographic source and the visible light cameras at the time when the visible light images were captured;

calculating radiographic geometry of each radiographic image relative to the radiographic source and the subject, wherein said calculation step comprises stereoscopic analysis of the at least two visible light images to determine relative positioning of the visible light cameras and the subject, and calculation of the radiographic geometry from the relative positioning and from the geometric relation between the radiographic source and the visible light cameras; and generating three-dimensional radiographic information on the subject by processing the one or more of radiographic images based on the radiographic geometry calculated in said calculating step.

22. A computer-readable medium according to claim 21, wherein the three-dimensional radiographic information includes stereoscopic x-ray images.

23. A computer-readable medium according to claim 21, wherein the three-dimensional radiographic information includes a tomosynthetic image at a designated slice depth into the subject.

24. A computer-readable medium according to claim 21, wherein the three-dimensional radiographic information includes a plurality of tomosynthetic images at a plurality of designated slice depths into the subject, and wherein the method performed by the process steps further comprises the step of reconstructing a volume of the subject by combining the plurality of tomosynthetic images.

25. A computer-readable medium according to claim 21, the method further comprising the step of registering one or more of the visible light images with the three-dimensional radiographic information.

26. A computer-readable medium according to claim 21, wherein the known geometric relation between the visible light cameras and the radiographic source is adjustable.

27. A computer-readable medium according to claim 21, wherein the three-dimensional radiographic information includes a radiographic volume reconstructed from the plural radiographic images.

28. A computer-readable medium according to claim 21, wherein the method performed by the process steps further comprise the steps of:

generating a surface topography of the subject by processing the visible light images; and registering the surface topography with the three-dimensional radiographic information.

29. A computer-readable medium according to claim 21, wherein at least two visible light cameras are used and wherein a first visible light camera is in a known geometric relation to the radiographic source and a geometric relation of a second visible light camera to the radiographic source is determined based on the known geometric relation of the first visible light camera to the radiographic source and a known geometric relation of the first visible light camera to the second visible light camera.

30. A computer-readable medium according to claim 21, wherein the three-dimensional radiographic information includes a zoom factor for correcting magnification error in at least one radiographic image.

31. A system for processing one or more radiographic images of a subject, comprising:

a radiographic source and sensor for acquiring the radiographic images of the subject;

one or more visible light cameras configured to capture at least two visible light images of the subject in correspondence to each radiographic image of the subject obtained by the radiographic sensor;

a memory for storing a geometric relation between the radiographic source and the visible light cameras at the time when the visible light images of the subject were captured; and a processor for calculating radiographic geometry of each radiographic image of the subject, wherein said calculation comprises stereoscopic analysis of the at least two visible light images to determine relative positioning of the visible light cameras and the subject, and calculation of the radiographic geometry from the relative positioning and from the geometric relation between the radiographic source and the visible light cameras, wherein said processor generates three-dimensional radiographic information on the subject by processing the one or more radiographic images based on the radiographic geometry.

32. A system according to claim 31, wherein the three-dimensional radiographic information includes stereoscopic x-ray images.

33. A system according to claim 31, wherein the three-dimensional radiographic information includes a tomosynthetic image at a designated slice depth into the subject.

34. A system according to claim 31, wherein the three-dimensional radiographic information includes a plurality of tomosynthetic images at a plurality of designated slice depths into the subject, and wherein said processor reconstructs a volume of the subject by combining the plurality of tomosynthetic images.

35. A system according to claim 31, wherein said processor registers one or more of the visible light images with the three-dimensional radiographic information.

36. A system according to claim 31, wherein the known geometric relation between said one or more visible light cameras and said radiographic source is adjustable.

37. A system according to claim 31, wherein the three-dimensional radiographic information includes a radiographic volume reconstructed from the plural radiographic images.

38. A system according to claim 31, wherein said processor generates a surface topography of the subject by processing the visible light images, and registers the surface topography with the three-dimensional radiographic information.

39. A system according to claim 31, wherein the three-dimensional radiographic information includes a zoom factor for correcting magnification error in at least one radiographic image.

40. A system according to claim 31, wherein at least two visible light cameras are used and wherein a first visible light camera is in a known geometric relation to the radiographic source and a geometric relation of a second visible light camera to the radiographic source is determined based on the known geometric relation of the first visible light camera to the radiographic source and a known geometric relation of the first visible light camera to the second visible light camera.

* * * * *

UNITED STATES PATENT AND TRADEMARK OFFICE
CERTIFICATE OF CORRECTION

PATENT NO. : 6,978,040 B2
DATED : December 20, 2005
INVENTOR(S) : Alexander L. Berestov It is certified that error appears in the above-identified patent and that said Letters Patent is hereby corrected as shown below:

Column 16,
Line 24, "tree-dimensional" should read -- three-dimensional --.

Signed and Sealed this

Twenty-third Day of May, 2006

JON W. DUDAS
*Director of the United States Patent and Trademark Office*